United States Patent [19]

Li

[11] Patent Number: 4,973,754

[45] Date of Patent: Nov. 27, 1990

[54] PREPARATION OF BIS(P-AMINOCUMYL)BENZENES

[75] Inventor: Simon M. Li, Houston, Tex.

[73] Assignee: Shell Oil Company, Houston, Tex.

[21] Appl. No.: 352,233

[22] Filed: May 15, 1989

[51] Int. Cl.$^5$ ............................................. C07C 211/00
[52] U.S. Cl. ..................................... 564/315; 564/330
[58] Field of Search ................................ 564/315, 330

[56] References Cited

U.S. PATENT DOCUMENTS

| | | | |
|---|---|---|---|
| 3,200,152 | 8/1965 | Ruppert | 260/570 |
| 4,303,551 | 12/1981 | Vaughan | 502/159 |
| 4,791,081 | 12/1988 | Childress | 502/62 |

FOREIGN PATENT DOCUMENTS

| | | | |
|---|---|---|---|
| 190101 | 8/1986 | European Pat. Off. | |
| 3309354 | 9/1989 | German Democratic Rep. | |
| 53-028128 | 3/1978 | Japan | |
| 60-081153 | 5/1985 | Japan | |
| 61-000044 | 10/1986 | Japan | |
| 61-238768 | 10/1986 | Japan | |
| 61-291549 | 12/1986 | Japan | |
| 62-132843 | 6/1987 | Japan | |
| 2155241 | 12/1987 | Japan | 564/315 |
| 2155242 | 12/1987 | Japan | 564/315 |
| 666167 | 6/1979 | U.S.S.R. | |

*Primary Examiner*—Richard L. Raymond
*Assistant Examiner*—Raymond Covington

[57] ABSTRACT

Bis(p-aminocumyl)benzenes are prepared by treating diisopropylbenzene derivatives with a primary or secondary aniline in the presence of a catalytic amount of an acidic perfluorinated polymer.

27 Claims, No Drawings

PREPARATION OF BIS(P-AMINOCUMYL)BENZENES

FIELD OF THE INVENTION

The present invention is directed to the preparation of bis(p-aminocumyl)benzenes.

BACKGROUND OF THE INVENTION

It is known to prepare bis(p-aminocumyl)benzene compounds by reacting an aniline with various substituted benzenes in the presence of activated clay or synthetic zeolites in Japanese patent application Nos. 61/000,044 and 62/155,241.

In the process, it is desirable to isolate the reaction medium from the catalyst in order to minimize product degradation during the subsequent removal at high temperatures of unconverted excess aniline. Particularly, when the catalyst is in the form of fine particles of acidic clay, this presents a major inconvenience for a filtration process and also limits the process to that of repetitive and tedious batch operations using fresh batches of catalyst.

Accordingly, there is a need to have effective catalysts for the preparation of bis(p-aminocumyl)benzenes which can also be practically utilized in continuous operations.

SUMMARY OF THE INVENTION

The present invention is directed to the preparation of a bis(p-aminocumyl)benzene by treating a diisopropylbenzene compound with a primary or secondary aniline in the presence of a catalytic amount of an acidic perfluorinated polymer.

The process is very efficient and, particularly in fixed-bed continuous operations where the catalyst can readily be isolated from the reaction medium which minimizes product degradation during subsequent high temperature aniline removal.

The catalysts for the process of the invention are acidic perfluorinated polymers. Such polymers, which can be used as catalysts, include those perfluorinated polymers that are prepared by conventional polymerization procedures known in the art from a perfluorinated precursor. The acidic perfluorinated polymer usually comprises a copolymer of an ethylenically unsaturated monomer, e.g., an alpha olefin, such as tetrafluoroethylene, ethylene, propylene or the like and perfluorinated monomers containing acid or precursor acid groups. The resulting copolymers can preferably contain from about 0.5 to about 50 mole percent of perfluorinated sulfonic acid groups. Suitable perfluorinated polymers include those disclosed in U.S. Pat. Nos. 4,303,551, 4,544,458, 4,626,553 incorporated by reference.

The perfluorinated polymers can be supported on a solid substrate for use in the process of the present invention. Suitable supports include organic or inorganic solids, including metallics, such as aluminum, monel, nickel, titanium, copper, brass, stainless steel (Hasteloy), tantalum, silicon carbide, glass, asbestos, zirconium, sulfonyl fluoride polymer, polyolefin, polyamide, polyester polymers, ceramic materials and the like and can optionally contain catalytically active metals, metal oxides, metal ions, metal chelates or other compounds which are catalytically active forms of the above-mentioned metals. The perfluorinated polymer can be incorporated onto (or in) the support by a variety of methods such as coextrusion, melt decomposition, deposition as a thin film and the like, including the procedures of U.S. Pat. Nos. 4,303,551 and 4,791,081 incorporated by reference. Preferably, the support is porous alumina or silicon carbide.

A preferred embodiment of the perfluorinated polymers of the invention is directed to perfluorinated polymers prepared by polymerizing at least two monomers, one of which is ethylenically unsaturated and the other is represented by a perfluorinated monomer as disclosed in U.S. Pat. No. 4,330,654, incorporated by reference.

For example, the solid perfluorinated polymer catalyst contains a repeating structure selected from the group consisting of:

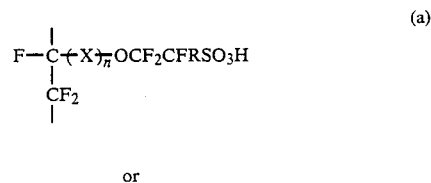

(a)

or

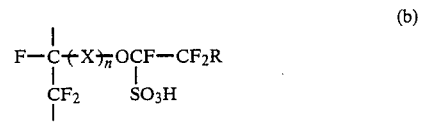

(b)

where n is 0, 1 or 2; R is a radical selected from the group consisting of fluorine and perfluoroalkyl radicals having from 1 to 10 carbon atoms; and X is selected from the group consisting of:

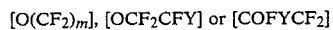

where m is an integer from 2 to 10 and Y is a radical selected from the class consisting of fluorine and the trifluoromethyl radical.

A preferred copolymer prepared by polymerizing perfluoroethylene with a perfluorovinyl ether containing attached sulfonic acid groups would have the following structure:

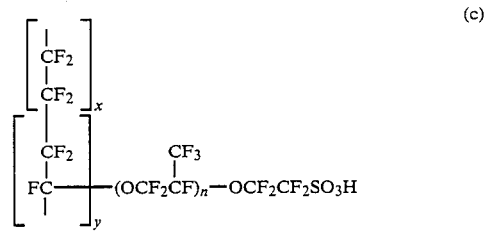

(c)

wherein $n=1$ or 2 and the ratio of x over y varies from about 2 to about 50. The polymer of structure (c) is available commercially under the tradename of NAFION® resin. Catalyst of the above-noted structure (c) offer the advantages of high concentrations of accessible acid groups in a solid phase.

The precise catalytic amount of the perfluorinated acidic polymer to be used will usually vary to some degree depending on the specific polymer, feed and conditions used for the process. By way of illustration, the catalyst can be present from about 0.05 lbs per lb of feed per hour to about 10.0 lbs per lb of feed per hour and preferably from about 0.2 lbs to about 2 lbs per lb of feed per hour.

Suitable diisopropylbenzene compounds include those of the formula I

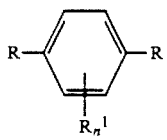

wherein R is isopropenyl or 2-hydroxyisopropyl; $R^1$ is an alkyl group containing 1 to 4 carbon atoms; and n is 0–4. For example, bis(p-(2-hydroxyisopropyl))benzene, bis(diisopropenyl)-benzene and ring alkylated derivatives thereof, preferably in which each $R^1$ is methyl or ethyl. Preferably, R is 2-hydroxyisopropyl or 2-isopropenyl and n is 0.

Suitable primary and secondary anilines include those of formula II

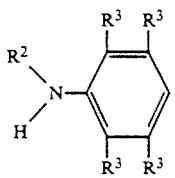

wherein $R^2$ is hydrogen, an alkyl, cycloalkyl, aryl or aralkyl group containing up to 10 carbon atoms, OH or $NO_3$; and $R^3$ is independently H, an alkyl group containing 1 to 4 carbon atoms or a halogen atom.

The reaction between the diisopropylbenzene compound and the aniline is usually conducted at elevated temperatures. Suitable temperatures are from about 80° C. to about 200° C. at ambient to slightly elevated pressures up to about 50 psig. Preferably, the reaction temperature is from about 100° C. to about 180° C. at ambient to about 25 psig. The pressure of the process is not critical but is conveniently from about ambient pressure to about 25 psig, although the use of higher or lower pressures is not excluded.

The reaction is conducted by contacting the reactants with the polymer catalyst for a period of time sufficient to effect the reaction depending on the feed rate, size of the polymer bed, reaction temperatures, the particular polymer used and the like and can readily be determined by those of skill in the art. By-product water is usually substantially removed during the course of or at the end of the reaction, e.g., by distillation or the like. Excess aniline reactant is removed by heating to a temperature of from about 120° C. to about 250° C. The resulting desired bis(p-aminocumyl)benzene product is then recovered by procedures such as flaking, solvent recrystallization and filtration and the like.

The ratio of diisopropylbenzene compound to aniline can vary. Usually an excess of aniline is desirable, generally from about 2 to about 20 moles per mole of diisopropylbenzene compound can be used, preferably from about 5 to about 15 moles of aniline per mole of diisopropyl benzene compound.

While the process of the invention can be conducted without a solvent, the process can be conducted in the presence of a non-basic solvent. Suitable solvents include hydrocarbons, alcohols, ketones and the like, such as toluene, methanol, acetone or the like.

Another embodiment of the invention is directed to a process comprising dehydrating a bis(p-(2-hydroxy-isopropyl))benzene in the presence of an acidic catalyst, removing the by-product water and treating the resulting diisopropenylbenzene with a primary or secondary aniline in the presence of an acidic perfluorinated polymer catalyst.

Any acidic dehydration catalyst can be used which is known in the art as effective for the dehydration of alcohols. Suitable catalysts include mineral acids, Lewis acids, cation exchange resin, acidic polymers, acidic clays and zeolites and the like. Preferably, the dehydration catalyst is an acidic clay or acidic polymer such as the perfluorosulfonic acid polymer described above, particularly if the solvent medium used in the dehydration step is the same primary or secondary aniline.

The dehydration reaction is usually conducted in solution using a suitable solvent a previously described above. The ratio of bis(p-(2-hydroxyisopropyl))benzene to dehydration catalyst depends on contact time, reaction temperature and the like, and can readily be determined by those of skill in the art. By way of example, the ratio of the bis(p-(2-hydroxyisopropyl))benzene in solution to dehydration catalyst is from about 0.2 to about 4 by weight per hour, preferably from 0.5 to about 1.5 per hour.

The temperature of the dehydration step is usually an elevated temperature. Suitable temperatures are from about 80° C. to about 180° C. at ambient or slightly elevated pressures of up to about 25 psig, preferably from about 100° C. to about 140° C.

By-product water is usually removed from the dehydration process by conventional techniques, e.g., by distillation or the like. The diisopropenylbenzene compound is recovered by conventional techniques such as isolation by evaporation of solvent, crystallization and filtration, or the like or can be used directly in the reaction with the primary or secondary aniline as above described, particularly if the solvent medium used in the dehydration step is the same primary or secondary aniline.

Those of skill in the art will appreciate that the process of the invention can be conducted as batch, continuous or semi-continuous process. The solid catalyst can be used as a slurry with the reactants in batch process or in a fixed-bed continuous process. The process can use equipment operated in series or in parallel.

ILLUSTRATIVE EMBODIMENTS

The invention is illustrated by the following embodiments which should not be regarded as limiting the invention in any way.

EMBODIMENT 1

Experiments were performed in batch using a 3:1 weight ratio of (a) dimethylaniline/bis(p-(2-hydroxyisopropyl))benzene mixture to (b) DOW XU-40036.01 perfluorocarbonsulfonic acid polymer on an alumina-based porous support at 350°–360° F. The ratio of dimethylaniline to bis(p-(2-hydroxyisopropyl))benzene was 10:1 M/M. Upon addition of the catalyst to the premix, heat was applied and the by-product water was azeotroped. Samples were taken when reaction temperature reached 350° F. and thereafter at set intervals. Samples were analyzed by high performance liquid chromatography (HPLC) at 280 nm. Results of these experiments are given in Table 1.

TABLE 1

| Catalyst | Reaction Time, Hr. | Product % Area, HPLC | % Normalized Area, HPLC |
|---|---|---|---|
| DOW XU-40036.01 | 0.00* | 0.22 | 5.33 |
| " | 0.23 | 0.45 | 13.08 |
| " | 0.5 | 1.11 | 33.37 |
| " | 1.0 | 3.58 | 68.95 |
| " | 2.03 | 16.58 | 88.98 |
| " | 3.16 | 24.90 | 90.87 |
| " | 4.25 | 24.48 | 90.02 |
| " | 6.08 | 22.32 | 88.47 |

*After H₂O removal and reaction temperature reached 350° F.

EMBODIMENT 2

Batch experiments were performed using a 3:1 weight ratio of (a) dimethylaniline/bis(p-isopropenyl)benzene mixture to (b) DOW XU-40036.01 perfluorocarbonsulfonic acid polymer on an alumina-based porous support at 350°-360° F. The ratio of dimethylaniline to bis(p-isopropenyl)benzene was 10:1 M/M. Results of these experiments are given in Table 2 where the samples were analyzed by high performance liquid chromatography (HPLC) similar to Embodiment 1.

TABLE 2

| Catalyst | Reaction Time, Hr. | Product % Area, HPLC | % Normalized Area, HPLC |
|---|---|---|---|
| DOW XU-40036.01 | 0 | 0 | — |
| " | 0.25 | 0.66 | 10 |
| " | 0.50 | 1.04 | 23.87 |
| " | 1.0 | 2.54 | 57.17 |
| " | 2.0 | 11.44 | 86.20 |
| " | 3.0 | 20.74 | 88.73 |
| " | 4.0 | 32.77 | 86.71 |
| " | 46.13 | 25.22 | 87.59 |

What is claimed is:

1. A process for the preparation of a bis(p-aminocumyl)benzene by treating a diisopropylbenzene compound with a primary or secondary aniline in the presence of a catalytic amount of an acidic perfluorinated polymer.

2. A process according to claim 1 wherein the aniline is aniline or a 2-alkylaniline or 2,6-dialkylaniline in which each alkyl contains from 1 to 4 carbon atoms.

3. A process according to claim 2 wherein the aniline is aniline, 2-methylaniline or 2,6-dimethylaniline.

4. A process according to claim 1 wherein the diisopropylbenzene compound is bis(p-(2-hydroxyisopropyl))benzene or bis(p-diisopropenyl)benzene.

5. A process according to claim 4 wherein bis(p-(2-hydroxyisopropyl))benzene is used.

6. A process according to claim 1 wherein the perfluorinated polymer is a copolymer of an ethylenically unsaturated monomer and a perfluorinated monomer containing acid or precursor acid groups.

7. A process according to claim 6 wherein the polymer contains from about 0.5 to about 50 moles percent of perfluorinated sulfonic acid groups.

8. A process according to claim 6 wherein the perfluorinated polymer contains a repeating structure selected from the group consisting of:

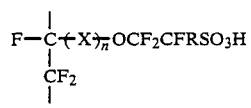
(a)

or

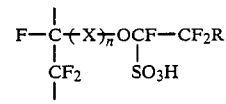
(b)

where n is 0, 1 or 2; R is a radical selected from the group consisting of fluorine and perfluoroalkyl radicals having from 1 to 10 carbon atoms; and X is selected from the group consisting of:

where m is an integer from 2 to 10 and Y is a radical selected from the class consisting of fluorine and the trifluoromethyl radical.

9. A process according to claim 9 wherein the polymer is prepared by polymerizing perfluoroethylene with a perfluorovinyl ether containing sulfonic acid groups and has the structure

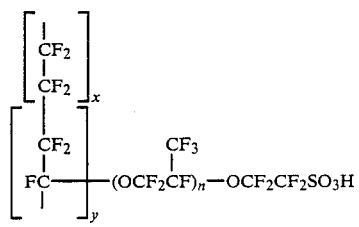

wherein n=1 or 2 and the ratio of x over y varies from about 2 to about 50.

10. A process according to claim 1 wherein the polymer is used with a solid support.

11. A process according to claim 5 wherein the support is porous alumina or silicon carbide.

12. The process according to claim 3 wherein bis(p-(2-hydroxyisopropyl))benzene is used.

13. The process according to claim 12 wherein the polymer is a copolymer of an ethylenically unsaturated monomer and a perfluorinated monomer containing sulfonic acid groups.

14. The process according to claim 13 wherein the polymer is used with a solid support.

15. A process for the preparation of a bis(p-aminocumyl)benzene which comprises dehydrating a bis(p-hydroxyisopropyl)benzene in the presence of an acidic catalyst, and treating the resulting diisopropenylbenzene with a primary or secondary aniline in the presence of an acidic perfluorinated polymer catalyst.

16. A process according to claim 15 wherein the dehydration catalyst is a mineral acid, a Lewis acid, acidic polymer, cation exchange resin, acidic clay or an acidic zeolite.

17. A process according to claim 16 wherein the dehydration catalyst is an acidic clay.

18. A process according to claim 17 wherein the aniline is aniline or a 2-alkylaniline or 2,6-dialkylaniline in which each alkyl contains from 1 to 4 carbon atoms.

19. A process according to claim 18 wherein the aniline is aniline, 2-methylaniline or 2,6-dimethylaniline.

20. A process according to claim 15 wherein the diisopropylbenzene compound is bis(p-(2-hydroxyisopropyl))benzene or bis(p-diisopropenyl)benzene.

21. A process according to claim 18 wherein bis(p-(2-hydroxyisopropyl))benzene is used.

22. A process according to claim 15 wherein an acidic polymer is used which is a perfluorinated copolymer of an ethylenically unsaturated monomer and a perfluorinated monomer containing acid or precursor acid groups.

23. A process according to claim 22 wherein the polymer contains from about 0.5 to about 50 moles percent of perfluorinated sulfonic acid groups.

24. A process according to claim 22 wherein the perfluorinated polymer contains a repeating structure selected from the group consisting of:

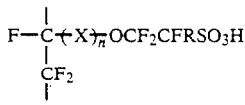
(a)

or

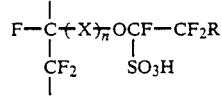
(b)

where n is 0, 1 or 2; R is a radical selected from the group consisting of fluorine and perfluoroalkyl radicals having from 1 to 10 carbon atoms; and X is selected from the group consisting of:

$[O(CF_2)_m]$, $[OCF_2CFY]$ or $[COFYCF_2]$ where m is an integer from 2 to 10 and Y is a radical selected from the class consisting of fluorine and the trifluoromethyl radical.

25. A process according to claim 24 wherein the polymer is prepared by polymerizing perfluoroethylene with a perfluorovinyl ether containing sulfonic acid groups and has the structure

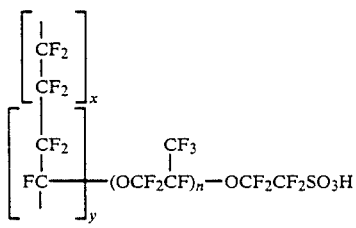

wherein n=1 or 2 and the ratio of x over y varies from about 2 to about 50.

26. A process according to claim 15 wherein the polymer is used with a solid support.

27. A process according to claim 6 wherein the support is porous alumina or silicon carbide.

* * * * *